(12) United States Patent
Lumgair, Jr. et al.

(10) Patent No.: US 7,495,141 B2
(45) Date of Patent: Feb. 24, 2009

(54) MINIMIZING CORROSION IN A METHANOL-TO-OLEFIN EFFLUENT PROCESSING SYSTEM

(75) Inventors: David R. Lumgair, Jr., Craddockville, VA (US); Jeffrey A. Kabin, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 10 days.

(21) Appl. No.: 11/787,334

(22) Filed: Apr. 16, 2007

(65) Prior Publication Data
US 2007/0197849 A1  Aug. 23, 2007

Related U.S. Application Data

(62) Division of application No. 10/603,716, filed on Jun. 25, 2003, now Pat. No. 7,208,648.

(51) Int. Cl.
*C07C 1/00* (2006.01)
*C07C 7/00* (2006.01)
*C07C 7/10* (2006.01)

(52) U.S. Cl. ............... 585/639; 585/640; 585/809; 585/833; 585/854; 585/860; 585/950

(58) Field of Classification Search ......... 585/638–640, 585/950, 809, 833, 854, 860; 210/900, 294, 210/252, 259
See application file for complete search history.

(56) References Cited

U.S. PATENT DOCUMENTS 6,403,854 B1 *  6/2002  Miller et al. ............... 585/638

* cited by examiner

*Primary Examiner*—In Suk Bullock

(57) ABSTRACT

The present invention is directed toward reducing corrosion in a methanol-to-olefin (MTO) effluent processing system, and particularly in the condensate removal system thereof, by injecting a neutralization agent into one or more target regions of the MTO effluent processing system. The neutralization agent ensures that any localized condensation in the MTO effluent processing system, particularly in the condensate removal system, occurs under basic conditions and that any acidic condensable components are neutralized. The invention is also directed to monitoring corrosion in an MTO effluent processing system and to monitoring the pH of localized corrosion sites in order to ensure proper neutralization of any acidic condensation formed therein.

18 Claims, 2 Drawing Sheets

MINIMIZING CORROSION IN A METHANOL-TO-OLEFIN EFFLUENT PROCESSING SYSTEM

CROSS REFERENCE TO RELATED APPLICATIONS

This application is a divisional of U.S. Ser. No. 10/603,716 filed Jun. 25, 2003 now U.S. Pat. No. 7,208,648 the entire contents of this application are herein incorporated by reference.

FIELD OF THE INVENTION

The present invention relates to minimizing corrosion in an effluent processing system, and more particularly to detecting and minimizing corrosion in a methanol-to-olefin effluent processing system by injecting a neutralization agent into one or more regions of the methanol-to-olefin effluent processing system.

BACKGROUND OF THE INVENTION

Light olefins such as ethylene and propylene are important commodity petrochemicals useful in a variety of processes for making plastics and other chemical compounds. Ethylene is used to make various polyethylene plastics, and in making other chemicals such as vinyl chloride, ethylene oxide, ethylbenzene and alcohol. Propylene is used to make various polypropylene plastics, and in making other chemicals such as acrylonitrile and propylene oxide. The petrochemical industry has known for some time that oxygenates, especially alcohols, are convertible into light olefins. The preferred conversion process is generally referred to as an oxygenate-to-olefin (OTO) reaction process. One particularly preferred OTO process is a methanol-to-olefins (MTO) reaction process, wherein methanol is converted to primarily ethylene and/or propylene in the presence of a molecular sieve catalyst.

Typically, the product stream from an MTO reactor is initially directed to a quench unit or tower for product quenching. In the quenching unit, the product stream contacts a quenching medium, usually water, under conditions effective to separate the product stream into a light product fraction and a heavy product fraction. The compounds in the product stream that are gaseous under the quenching conditions are separated therefrom as the light product fraction. The light product fraction typically contains light olefins, dimethyl ether, methane, CO, $CO_2$, ethane, propane, and other minor components such as water and unreacted oxygenate feedstock. The light product fraction is compressed and directed to olefin product recovery and purification. The compounds in the product stream that are liquid under quenching conditions, are separated therefrom as the heavy product fraction. The heavy product fraction contains byproduct water, a portion of the unreacted oxygenate feedstock (except those oxygenates that are gases under quenching conditions), a small portion of the oxygenate conversion byproducts, particularly heavy hydrocarbons (C5+), and usually the bulk of the quench medium. The heavy product fraction may be processed to separate one or more of the heavy components contained therein. Exemplary non-limiting MTO separation systems are described in U.S. Pat. No. 6,121,504 and U.S. Pat. No. 6,482,998, the entireties of which are incorporated herein by reference and in U.S. patent application Ser. No. 10/383,204, filed Mar. 6, 2003, and U.S. patent application Ser. No. 10/292,232, filed Nov. 12, 2002, the entireties of which are also incorporated herein by reference.

Various byproducts are produced in the MTO reaction process. These byproducts may include organic or inorganic acids in the C1 to C6 range. These acids exit the MTO reactor in an MTO reaction effluent, which also includes the desirable light olefins formed in the MTO reaction process. A significant amount of carbon dioxide, which forms carbonic acid when dissolved in water, may also be present in the reaction effluent. These acidic components are usually divided between the light product fraction and the heavy product fraction. As a result, both the light and heavy product fractions are considerably acidic.

It has now been discovered that the acidity in the light and heavy fractions can cause localized corrosion in various regions of an MTO effluent processing system. Corrosion can reduce the thickness of pipe walls, ultimately leading to pipe weakening and failure, particularly at high pressures. Thus, the need exists for reducing corrosion in an MTO effluent processing system.

SUMMARY OF THE INVENTION

This invention provides processes and systems for detecting and reducing corrosion in various regions of a methanol-to-olefin (MTO) effluent processing system. In one embodiment the invention is directed to a process for minimizing corrosion in an MTO effluent processing system, particularly in a pumparound stream of an MTO quench unit. According to this embodiment, a product stream is directed from an MTO reactor to a quench unit through a quench unit inlet. The product stream contacts a quench medium in the quench unit under conditions effective to form a light product fraction containing light olefins, a heavy product fraction containing condensed components, and a condensed pumparound stream. A neutralization agent is added to the condensed pumparound stream to form the quench medium, wherein the quench medium has a pH greater than the pH of the condensed pumparound stream. The quench medium is injected into the quench unit at an injection point oriented higher on the quench unit than the quench unit inlet. Optionally, the pH of the condensed pumparound stream is monitored and the neutralization agent is added responsive to a determination that the pH of the pumparound stream is approaching acidic conditions.

In another embodiment, the invention is directed to a process for reducing corrosion in an MTO reactor system, and particularly in an MTO quench unit overhead stream. In this embodiment, a product stream from an MTO reactor contacts a quench medium in a quench unit under conditions effective to form an overhead stream comprising light olefins and a bottoms stream comprising the quench medium and condensed oxygenates. A portion of the overhead stream is condensed to form a condensed stream having a pH. A neutralization agent contacts the condensed stream to form a treated stream having a pH greater than the pH of the condensed stream.

According to one embodiment, corrosion is reduced in an MTO effluent processing system, and particularly in the compression system thereof. In this process, a product stream from an MTO reactor contacts a quench medium in a quench unit under conditions effective to form an light product fraction comprising light olefins and a heavy product fraction comprising the quench medium and condensed oxygenates. At least a portion of the light product fraction is compressed to form a compressed stream. At least a portion of the compressed stream is cooled under conditions effective to form a condensed stream having a pH. A neutralization agent contacts at least a portion of the condensed stream to form a treated stream having a pH greater than the pH of the condensed stream.

In another embodiment, the present invention is a process for reducing corrosion in an MTO reactor system, and particularly in a reboiler system thereof. The process includes contacting a product stream from an MTO reactor with a quench medium in a quench unit under conditions effective to form a first overhead stream and a first bottoms stream, wherein the first overhead stream comprises light olefins, and wherein the first bottoms stream comprises the quench medium and condensed oxygenates. At least a portion of the first bottoms stream is directed to a condensate stripper and heated in the condensate stripper under conditions effective to form a second overhead stream and a second bottoms stream. The second overhead stream contains recovered oxygenates, and the second bottoms stream contains stripped quench medium. At least a portion of the second bottoms stream is partially vaporized to form a vaporized phase and a liquid phase having a pH. A neutralization agent is added to the liquid phase to form a treated stream having a pH greater than the pH of the liquid phase.

In yet another embodiment, the invention is directed to a process for reducing corrosion in an MTO effluent processing system, and particularly in the overhead stream of a condensate stripper. This process includes contacting a product stream from an MTO reactor with a quench medium in a quench unit under conditions effective to form a first overhead stream and a first bottoms stream. The first overhead stream comprises light olefins, and the first bottoms stream comprises the quench medium and condensed oxygenates. At least a portion of the first bottoms stream is directed to a condensate stripper. The at least a portion of the first bottoms stream in the condensate stripper is heated under conditions effective to form a second overhead stream and a second bottoms stream. The second overhead stream contains recovered oxygenates, and the second bottoms stream contains stripped quench medium. The second overhead stream is cooled under conditions effective to partially condense the second overhead stream and form a condensed stream having a pH. A neutralization agent contacts the condensed stream to form a treated stream, wherein the treated stream has a pH greater than the pH of the condensed stream.

The invention is also directed to detecting corrosion and neutralizing acidic condensation sites in an MTO effluent processing system. In one embodiment, the invention is a process for reducing corrosion of a conduit line having an inner surface. The process includes directing a first stream having a pH through the conduit line, wherein the conduit line is a component of an MTO effluent processing system. Corrosion in the conduit line is monitored. A neutralization agent is injected through an inlet in the conduit line to form a treated stream having a pH greater than the pH of the first stream. The injecting step is responsive to a determination in the monitoring step that corrosion has developed at a corrosion point in the conduit line. The inlet preferably is oriented upstream of the corrosion point.

In another embodiment, the invention is a process for reducing corrosion in an MTO effluent processing system, and particularly in a single or a multiple pumparound stream of an MTO quench unit. The process includes contacting a product stream from an MTO reactor with a quench medium in a quench unit under conditions effective to form an overhead stream and a bottoms stream, wherein the overhead stream contains light olefins, and wherein the bottoms stream contains water and condensed oxygenates. Condensed components having a pH are withdrawn from the quench unit through a first outlet in the quench unit. A first neutralization agent contacts the condensed components to form a first treated stream, wherein the first treated stream has a pH greater than the pH of the condensed components. The first treated stream is introduced into a first inlet in the quench unit, wherein the first inlet is located at a position higher on the quench unit than the first outlet. The first treated stream acts as the quench medium in the contacting step. Optionally, the process includes withdrawing additional condensed components having a pH from the quench unit through a second outlet in the quench unit, wherein the second outlet is located at a position higher on the quench unit than the first outlet. The additional condensed components are introduced into a second inlet in the quench unit, wherein the second inlet is located at a position higher on the quench unit than the second outlet, and wherein the additional condensed components act as the quench medium.

In one embodiment, the invention is a process for reducing corrosion in a conduit line having an inner surface. The process includes directing a first stream having a pH through the conduit line, wherein the conduit line is part of an MTO effluent processing system. The pH of the first stream is monitored, and a neutralization agent contacts the first stream to form a treated stream having a pH greater than the pH of the first stream. The contacting is responsive to a determination in the monitoring that the pH of the first stream has passed a predetermined threshold.

In another embodiment, the invention is a process for reducing corrosion in an MTO effluent processing system, and particularly in a condensed pumparound stream. The inventive process includes directing a product stream from an MTO reactor to a condensing unit through a condensing unit inlet. The product stream contacts a treated stream in the condensing unit under conditions effective to form a light product fraction containing light olefins, a heavy product fraction containing condensed components, and a condensed pumparound stream. A neutralization agent is added to the condensed pumparound stream to form the treated stream, wherein the treated stream has a pH greater than the pH of the condensed pumparound stream. The treated stream is injected into the condensing unit at an injection point oriented higher on the condensing unit than the condensing unit inlet.

BRIEF DESCRIPTION OF THE DRAWINGS

This invention will be better understood by reference to the Detailed Description of the Invention when taken together with the attached drawings, wherein.

DETAILED DESCRIPTION OF THE INVENTION

Introduction

Figure 1:
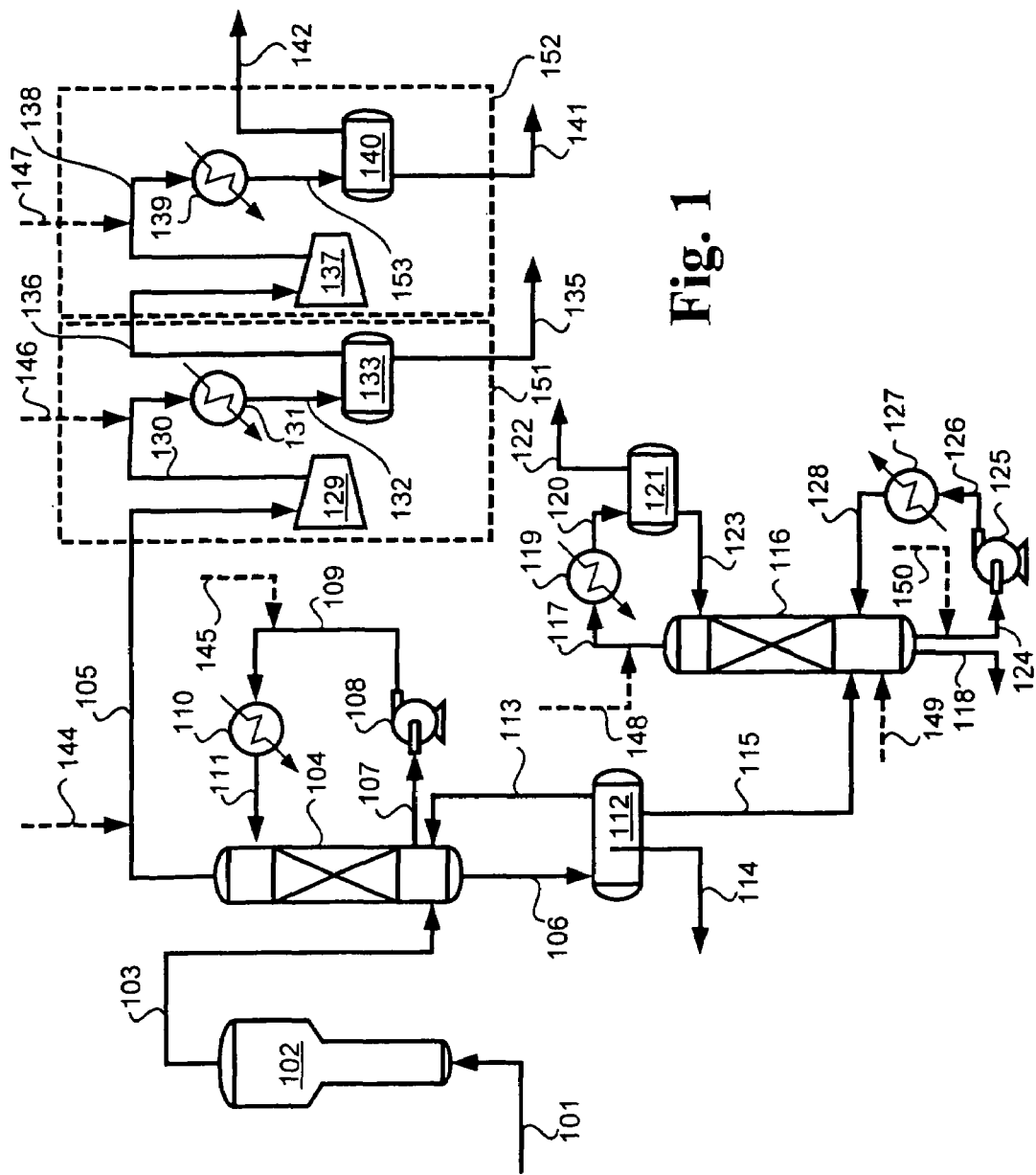
FIG. 1 illustrates a methanol-to-olefin reactor and condensate removal system according to one embodiment of the present invention.

The invention is directed toward reducing corrosion in a methanol-to-olefin (MTO) effluent processing system. More specifically, the present invention provides for reducing corrosion in an MTO effluent processing system by injecting one or more neutralization agents into various target regions in the MTO effluent processing system that are susceptible to the formation of localized condensation having a pH less than 7.0. The neutralization agent ensures that any localized condensation in the MTO effluent processing system occurs under basic conditions and that any acidic condensable components are neutralized. The invention is also directed to monitoring corrosion in an MTO effluent processing system and to monitoring the pH of localized condensation sites in order to ensure proper neutralization of any acidic components contained therein.

Processes for Reducing Corrosion

The present invention is directed to reducing corrosion in one or more regions of an MTO effluent processing system. Preferably, corrosion is reduced by injecting one or more neutralization agents into the regions of an MTO effluent processing system that are susceptible to corrosion.

An MTO reaction effluent typically contains light olefins, byproduct water and various other byproducts. The water and some of the byproducts may be removed from the reaction effluent by implementing a condensate removal system in the MTO effluent processing system, discussed in more detail below with reference to FIG. 1 and FIG. 2. The condensate removal system preferably is adapted to remove at least a portion of the condensable components, e.g., water, from an initial product stream received from an MTO reactor. The condensate removal system may include one or more quench units, one or more compressors each stage of which preferably includes a corresponding heat exchanger and knockout drum, and one or more condensate strippers, preferably distillation columns, which are adapted to remove condensable components. Various conduit lines, e.g., pipes, direct the product stream from the MTO reactor to the one or more quench units, compressor stages, knockout drums, and condensate strippers.

More specifically, after the product stream exits the MTO reactor, it preferably is directed to a quench unit, e.g., a quench tower. Preferably, the quench unit contains packing material and/or trays to facilitate product quenching. In the quench unit, the product stream contacts a quench medium, preferably in a countercurrent manner, under conditions effective to separate at least a portion of the condensable components in the product stream from lighter less-condensable components. The components in the product stream that are gaseous under quenching conditions are removed from the quench unit as a light product fraction and are subsequently directed to olefin product recovery and purification. The light product fraction comprises light olefins, dimethyl ether, methane, carbon monoxide, carbon dioxide, ethane, propane and other minor components such as water and unreacted oxygenate feedstock. The compounds in the product stream that are liquids under quenching conditions are removed from the quench unit as a heavy product fraction for possible division into several fractions and separation of the quench medium. The heavy product fraction contains byproduct water, a portion of the unreacted oxygenate feedstock (except those oxygenates that are gases under quenching conditions), a small portion of the oxygenate conversion byproducts, particularly heavy hydrocarbons ($C_5+$), and usually the bulk of the quench medium.

Preferably, the quench medium is selected from a composition that remains substantially as a liquid under the quenching conditions, thus minimizing the amount of the quench medium present in the light product fraction, which must undergo more expensive gaseous product processing steps to recover commercially acceptable grades of light olefin products. A preferred quench medium is selected from the group consisting of water and streams that are substantially water. More preferably, the quench medium is a stream that is substantially water and is selected from the several fractions of the heavy product fraction from the quench unit. Preferably, some condensed components are collected in one or more trays within the quench unit, and a pump removes a portion of the condensed components, from a first outlet in the quench unit, thus forming a pumparound stream. This portion of the condensed components serves as the quench medium, referred to above. The first outlet preferably is oriented lower on the quench unit than the inlet that receives the product stream from the MTO reactor. The pumparound stream is cooled prior to being reintroduced into the quench unit at a first inlet oriented higher on the quench unit than the first outlet. This pumparound stream facilitates product quenching by cooling the product stream in the quench unit.

Optionally, the quench unit includes a plurality of pumparound streams, e.g., two, three, four or more pumparound streams. In this embodiment, condensed components may be withdrawn from the quench unit through one or more outlets in the quench unit. In one embodiment, a single condensed stream containing condensed components is removed from the quench unit through a first outlet, e.g., a single bottoms stream outlet or a single side draw stream outlet. The single condensed stream preferably is cooled in one or more heat exchangers and divided into two or more derivative condensate streams. The one or more heat exchangers preferably are plate-and-frame and/or shell-and-tube type heat exchangers. If the quench unit includes two pumparound streams, then the single condensed stream is cooled and divided into a first derivative condensate stream and a second derivative condensate stream. The first derivative condensate stream preferably is introduced into a first inlet in the quench unit, which is oriented higher on the quench unit than the first outlet. The first derivative condensate stream then serves as a first quench medium in the quench unit and facilitates the condensing of condensable components contained therein. The second derivative stream optionally is cooled further in a second heat exchanger and introduced into a second inlet in the quench unit. Ideally, the second inlet is oriented higher on the quench unit than the first outlet and the first inlet. The second condensate stream serves as a second quench medium in the quench unit and also facilitates the condensing of condensable components contained therein.

In another embodiment, the quench unit includes a plurality of pumparound streams withdrawn from a plurality of outlets. In this embodiment, condensed components are withdrawn from the quench unit through one or more side draw stream outlets, and, optionally, through a bottoms stream outlet. For example, a first condensate stream optionally is withdrawn from a first outlet on the quench unit, e.g., the bottoms stream outlet, and is cooled in a heat exchanger to form a first cooled pumparound stream. The first cooled pumparound stream preferably is introduced into a first inlet in the quench unit. The first cooled pumparound stream serves as a first quench medium in the quench unit and facilitates the condensing of condensable components contained therein. A second condensate stream optionally is withdrawn from a second outlet on the quench unit, which preferably is oriented higher on the quench unit than the first outlet and the first inlet, and is cooled in a heat exchanger to form a second cooled pumparound stream. The second cooled pumparound stream ideally is cooled to a lower temperature than the first cooled pumparound stream. The second cooled pumparound stream is introduced into a second inlet in the quench unit, which is oriented higher on the quench unit than the second outlet. Thus, the second inlet also preferably is oriented higher on the quench unit than the first outlet and the first inlet. The second cooled pumparound stream serves as a second quench medium in the quench unit and also facilitates the condensing of condensable components contained therein.

The heavy product fraction may contain three phases: a vapor phase containing volatile light components, an aqueous phase containing mostly water, and an oil phase, which typically is less dense than the aqueous phase and floats thereon. In one embodiment of the condensate removal system, the heavy product fraction from the quench unit is directed to a three-phase separation unit wherein the heavy product fraction is subjected to conditions effective to separate the heavy product fraction into a vapor phase, an oil phase and an aqueous phase. The three-phase separation unit preferably is a knockout drum having a vapor stream outlet, an aqueous outlet and an oil outlet, which ideally is an opening in a conduit that extends through the heavier aqueous layer and withdraws the oil phase from a point above the oil/aqueous interface. Optionally, the three-phase separation unit is integral with the quench unit. In this embodiment, the three-phase separation unit is included in the bottom of the quench vessel below a pumparound drawoff tray. The vapor stream typically contains light components such as water vapor, light hydrocarbons (C3-), light oxygenates, light olefins, and unreacted methanol. The oil stream typically contains heavier aromatic compounds. The vapor in the vapor stream preferably is redirected to the quench unit for further processing, and the oil in the oil stream preferably is directed to one or more separation units for further processing or is burned as fuel. The aqueous stream typically contains water, unreacted oxygenates such as methanol And dimethyl ether, as well as aldehydes, organic and inorganic acids, and dissolved hydrocarbons. The aqueous phase preferably is directed to a condensate stripper in order to recover any unreacted oxygenates therefrom.

The condensate stripper preferably is a distillation column, which is adapted to separate unreacted oxygenates from water. In one embodiment of the present invention, the condensate stripper is a packed column capable of removing at least about 90 weight percent, more preferably at least about 95 weight percent, more preferably at least about 99 weight percent, and most preferably at least about 99.9 weight percent of the methanol from the one or more streams that are directed thereto, based on the total weight of the one or more streams. The condensate stripper also preferably is capable of removing at least about 90 weight percent, more preferably at least about 95 weight percent, more preferably at least about 99 weight percent, and most preferably at least about 99.9 weight percent of the DME that was present in the one or more streams that were directed to the condensate stripper, based on the total weight of the one or more streams. In the condensate stripper, the aqueous stream from the three-phase separation unit preferably is subjected to conditions, e.g., temperature and pressure, effective to form an overhead oxygenate stream, which contains a majority of the oxygenates that were present in the aqueous stream, and a stripped water-containing stream, which preferably contains a majority of the water that was present in the aqueous stream. If the quenching system does not include a three-phase separation unit, then the heavy product fraction, or a portion thereof, optionally is directed to the condensate stripper for formation of the overhead oxygenate stream and the stripped water-containing stream, which contain majorities of the oxygenates and water, respectively, that were present in the heavy product fraction.

Preferably, the condensate stripper includes an overhead condenser system for forming the overhead oxygenate stream. In this embodiment, at least a portion of an initial overhead stream from the condensate stripper is directed to one or more heat exchangers for initial overhead stream cooling. The one or more heat exchangers preferably are shell-and-tube type exchangers, wherein at least a portion of the initial overhead stream directly or indirectly contacts a cooling medium under conditions effective to cool at least a portion of the initial overhead stream, thus forming a cooled overhead stream. The cooled overhead stream is then directed to a knockout drum wherein condensable components are allowed to condense. The condensed components in the knockout drum preferably are withdrawn therefrom via a condensate outlet and are redirected to the condensate stripper for further processing. Non-condensable components, e.g., gaseous components, form the overhead oxygenate stream and are withdrawn from the knockout drum via a vapor outlet. At least a portion of the overhead oxygenate stream preferably is directed to the MTO reactor for further conversion to light olefins. Optionally, all or substantially all of the components in the cooled overhead stream are condensed to form a condensed stream, and a portion of the condensed stream is redirected to the MTO reactor for further conversion to light olefins.

The condensate stripper also preferably includes a reboiler system. In this embodiment, an optional pump withdraws a stripped reboiler stream, e.g., a bottoms stream, from the condensate stripper and directs the stripped reboiler stream to one or more heat exchangers for stripped reboiler stream heating. As used herein, the terms "bottoms stream" and "overhead stream" are not limited to bottoms and overhead streams, respectively, but also encompass side draw streams oriented adjacent the bottom or top of the processing unit being described. Alternatively, a thermosiphon rather than a pump is used to withdraw the stripped reboiler stream from the condensate stripper. The one or more heat exchangers preferably are shell-and-tube type exchangers, wherein at least a portion of the stripped reboiler stream directly or indirectly contacts a heating medium under conditions effective to heat, preferably vaporize, at least a portion of the stripped reboiler stream, thus forming a heated reboiler stream. At least a portion of the heated reboiler stream is then redirected to the condensate stripper for further processing. Optionally, a single bottoms stream is withdrawn from the condensate stripper and is divided between the stripped water-containing stream and the stripped reboiler stream. Alternatively, two bottoms streams are withdrawn in parallel from the condensate stripper, as shown in FIG. 1, the first stream being the stripped water-containing stream and the second stream being the stripped reboiler stream.

The light product fraction from the quench unit preferably is directed to a compression system. The compression system preferably includes one or more compressor units or bodies, which are adapted to compress at least a portion of the light product fraction. The compression system also preferably includes one or more intercoolers and knockout drums. The compressor system has the dual purpose of facilitating the movement of the light product fraction through the MTO effluent processing system as well as condensing out heavier less-desirable components from the light product fraction.

Compressors such as centrifugal compressors ideally are implemented in the compression system. These compressors are often formed of a body having one or more stages. Each stage has a respective inlet and outlet and usually includes one or more sections, each having an impeller and a diaphragm. Each stage also preferably includes an intercooler and a knockout drum. In many instances, multiple bodies and stages are used. To reduce the power required to drive these multiple stages, intercoolers are often placed between them. An intercooler is a heat exchanger situated immediately downstream from a compressor. In some cases, intercoolers are also used between stages to reduce the power required for compression.

In one embodiment of the present invention, compressors act to compress at least a portion of the light product fraction thereby forming a compressed light product stream. The compressed light product stream is directed to one or more intercoolers. As the compressed light product stream is cooled in the intercoolers, readily condensable components preferably condense out of the compressed light product stream. The one or more intercoolers preferably are shell-and-tube type exchangers, wherein at least a portion of the compressed light product stream directly or indirectly contacts a cooling medium under conditions effective to cool at least a portion of the compressed light product stream, thereby forming a cooled light product stream. The cooled light product stream is then directed to a knockout drum wherein the readily condensable components are allowed to condense. Condensed aqueous components in the knockout drum preferably are withdrawn therefrom via at least one condensate outlet thus forming an aqueous condensate stream. An oil layer may form on top of the condensed aqueous condensate layer. If so, then the knock out drum preferably is a three-phase separation unit adapted to separate the three phases contained therein. Optionally, a portion or all of the aqueous condensate stream is directed to and combined with the pumparound stream associated with the quench unit. Preferably, however, a portion or all of the aqueous condensate stream is directed to and introduced into the quench unit for further processing. Desirably, the compression system includes a plurality of compression stages, more preferably at least 2, 3, 4, 5 or more compression stages. If the compression system includes a plurality of compression stages, then a portion or all of the aqueous condensate stream from a given knockout drum optionally is directed to and combined with one or more upstream and/or downstream compressed light product streams and/or cooled light product streams.

Non-condensable components, e.g., gaseous components, form a derivative light product stream and are withdrawn from the knockout drum via a vapor outlet. At least a portion of the derivative light product stream preferably is directed to additional compressor stages, as described above, for further compression and removal of readily condensable components and thereby forming additional derivative light product fractions and, ultimately, a final light product stream. After exiting the compression system, the final light product stream preferably is directed to a separation system for removal of light ends such as methane, hydrogen, and carbon monoxide, in addition to removal of DME, ethane and propane and other minor components. Ideally, the separation system isolates polymerization grade ethylene and propylene from the final light product stream. Any of a number of various separation schemes and recovery trains may be implemented to separate the various components in the final light product fraction.

It has now been discovered that conditions may be favorable in an MTO effluent processing system, and particularly in a condensate removal system, to form localized acidic condensation. The condensation may contain one or more undesirably acidic components, such as, but not limited to, acetic acid, formic acid, carbonic acid, and various heavy organic acids. Depending on the concentration of these acidic components, localized condensation in the condensate removal system may be undesirably acidic having a pH less than 7.0. Locally, the pH of the condensation may be as low as 3.0 or 2.0. As a result, the condensation is likely to lead to corrosion of steel or low alloy surfaces, e.g., pipe surfaces, within the MTO effluent processing system or the condensate removal system thereof. The present invention is directed to reducing or eliminating corrosion in an MTO effluent processing system, and particularly in the condensate removal system thereof, by injecting one or more neutralization agents into the regions of the MTO effluent processing system that are prone to localized acidic condensation and, correspondingly, to regions where corrosion is likely to pose a problem. By injecting a neutralization agent into these target regions of the condensate removal system, conditions can be maintained basic where necessary and a commensurate decrease in corrosion can be advantageously realized. Upon addition of the neutralization agent, a treated stream is formed, which preferably has a pH of at least 6.0, more preferably at least 7.0, optionally at least 8.0, and optionally from about 7.0 to about 8.0.

It has now been discovered that acidic condensation forms in the quench unit of an MTO effluent processing system. One embodiment of the present invention is directed to reducing corrosion in the quench unit and/or in the one or more pumparound streams thereof by injecting a neutralization agent and/or into the quench unit into one or more regions of the quench unit pumparound. In a particularly preferred embodiment, the neutralization agent is injected into one or more regions of the quench unit pumparound stream(s). Each pumparound stream includes a pump, a heat exchanger, and conduit lines. The pump withdraws the condensed components (e.g., the quench medium) from the quench unit, directs the condensed components through a conduit and one or more heat exchangers, and returns the cooled condensed components through another conduit and into the quench unit to serve as the quench medium. The neutralization agent may be injected into any one or more of these regions of the pumparound stream. If the quench unit includes a plurality of pumparound streams, then the neutralization agent may be injected into one, more or all of these regions in one or more of the pumparound streams. In another embodiment, the neutralization agent is injected directly into the quench unit without mixing the neutralization agent with the quench medium prior to the introduction of the neutralization agent into the quench unit. In this latter embodiment, the injection point preferably is higher on the quench unit than the introduction point of the stream to be processed by the quench unit, e.g., the product stream from the MTO reactor. If the quench unit contains packing material or trays, then the neutralization agent optionally is injected directly into the region of the quench unit that contains the packing material or trays, above the packing material or trays, or below the packing material or trays.

Acidic condensation has also been detected in the condensate stripper and the condenser and reboiler systems associated therewith. To reduce corrosion in the condenser system, in one embodiment of the present invention, the neutralization agent is injected into one or more regions within the condenser system associated with the condensate stripper. The condenser system includes an initial overhead stream and a heat exchanger, which cools the initial overhead stream to form a cooled overhead stream. The condenser system also optionally includes a knockout drum, and one or more condensed component streams. The neutralization agent may be injected into any one or more of these locations within the condenser system. The neutralization agent also may be injected into one or more overhead oxygenate streams which receive vaporized oxygenate components form the knockout drum.

In another embodiment, the invention is directed to reducing corrosion in the condensate stripper itself. In this embodiment, the neutralization agent is injected into one or more regions of the condensate stripper. The neutralization agent preferably is injected into the condensate stripper in a region below the introduction point of the stream to be stripped, e.g., the heavy product fraction from the quench unit or a portion thereof such as an aqueous stream from the three-phase separation unit. Additionally or alternatively, the neutralization agent may be injected into the condensate stripper at a point above this introduction point. The neutralization agent optionally is injected directly into the region of the condensate stripper that contains the packing material or trays, above the packing material or trays, or below the packing material or trays. In another embodiment, the neutralization agent is injected into the aqueous stream and/or into the heavy product fraction prior to its introduction into the condensate stripper.

In another embodiment of the present invention, the neutralization agent is injected into one or more regions within the reboiler system of the condensate stripper, thereby reducing corrosion in this region. The reboiler system includes an optional pump, a heat exchanger, and the conduit lines that withdraw the reboiler bottoms stream from the condensate stripper, direct the stream to the heat exchanger and direct the heated reboiler stream back to the condensate stripper for further processing. The neutralization agent may be injected into any one or more of these locations of the reboiler system.

In another embodiment of the present invention, the neutralization agent is injected into one or more regions of the compression system. Specifically, the neutralization agent optionally is injected into one or more of: the light product fraction, one or more of the compressor units, the compressed light product stream(s), the intercooler(s), the cooled light product stream(s), the knockout drum(s), the quench recycle stream(s), if any, the condensate stream(s), derivative light product stream(s), and the final light product stream.

According to the present invention, a variety of neutralization agents may be implemented to decrease the acidity of the one or more localized condensation points. The neutralization agent should be basic, having a pH greater than 7.0, more preferably greater than about 9.0, and most preferably greater than about 11.0. Optionally, the neutralization agent is selected from the group consisting of: caustic, ammonium hydroxide, potassium hydroxide, ammonia and amines. Filming amines such as those marketed by NALCO are preferred neutralization agents in regions where localized corrosion occurs in conduits that transport mostly vapor, e.g., the light product fraction from the quench unit. In one preferred embodiment, the neutralization agent is an aqueous basic solution. Preferably, the neutralization agent comprises substantially no sulfur. Ideally, the neutralization agent contains less than about 10,000 wppm, preferably less than about 100 wppm, more preferably less than about 1 wppm, and most preferably an undetectable amount of sulfur, defined herein as less than 0.01 wppm sulfur.

Preferably, the neutralization agent injection system includes a pump, such as a positive displacement pump, a metering pump or a piston pump, that is capable of providing a known neutralization agent injection rate. The pump withdraws neutralization agent from a storage tank, in which the neutralization agent is stored, and directs the neutralization agent through one or more conduits to one or more delivery devices adjacent one or more target regions of the effluent processing system. Ideally, the delivery device is an injection means, e.g., an atomizing device such as a nozzle, that is capable of injecting droplets of the neutralization agent within the target region. However, a variety of injection means may be used to inject the neutralization agent into the one or more target regions. In another embodiment, the injection means forms a basic coating on the one or more metal surfaces within the target region.

The injection flow rate may vary widely based on a variety of factors such as, but not limited to, the product fraction flow rate in the target region, the pH of the neutralization agent, the pH of the condensation in the target region, and the amount of condensate in the target region. A portion of the neutralization agent may vaporize as it is injected into the target region. However, vaporization is undesirable as the neutralization properties of the neutralization agent are reduced if the neutralization agent is in the vapor phase. Thus, the injection rate of the neutralization agent preferably is selected so that at least a portion of the neutralization agent is in the liquid phase after it is injected into the target region. Similarly, the temperature and pressure of the neutralization agent preferably is selected so that at least a portion of the neutralization agent is maintained in a liquid phase. Preferably, the temperature of the neutralization agent is less than about 300° F. (149° C.), more preferably less than about 150° F. (66° C.), and most preferably less than about 120° F. (49° C.). In another embodiment, the flow rate can vary depending on the degree of acidity of the condensation detected in the target region. Generally, the more acidic the detected condensation, the greater the flow rate.

As indicated above, as acidic condensation develops, corrosion will occur on metal surfaces that contact the condensation. This corrosion, if left uncorrected, can lead to conduit weakening, decreased heat exchanger lifetime, decreased compressor efficiency and, ultimately, to compressor and/or conduit failure. In one embodiment of the present invention, the condensation in one or more regions of the MTO compressors is monitored either by a pH detection device, e.g., a pH meter, titration, liquid analysis, or litmus paper, or by less sophisticated means, e.g., by inserting and monitoring one or more corrosion coupons within the target region. A corrosion coupon is a piece of metal, which, when inserted into a pipe, compressor, heat exchanger or other device will gradually corrode in an acidic environment. The coupon preferably can be withdrawn from the target region for periodic analysis to determine whether the target region is susceptible to the development of corroding condensation. Preferably, the corrosion coupon is formed of the same material or a less-acid-resistant material than the metal used to form the target region itself. Depending on the target region being monitored, the one or more corrosion coupons may be pulled and analyzed, for example, from once every week to 3 years or more, preferably once every 6 months to 3 years. In this embodiment, as corrosion is detected, the neutralization agent can be intermittently injected into the target region, preferably up-stream of the pH detection device or the corrosion coupon, on an as-needed basis. The intermittent injecting preferably is responsive to a determination in the monitoring that corrosion in the target region has exceeding a predetermined level. If a pH meter is used, then the injecting preferably is responsive to a determination in the monitoring that the pH of the target region is approaching or has reached acidic conditions. Ideally, however, the compressors operate above the dew point to minimize corrosion.

Preferably, the neutralization agent is continuously injected into the one or more target regions. The injection rate can be varied based on the determinations made in the monitoring steps in order to optimize the amount of neutralization agent used while satisfactorily minimizing corrosion.

In another embodiment, the neutralization agent is injected into the target region or regions intermittently at prescheduled intervals. The interval between injections may vary based on a number of factors such as the acidity of the condensation in the target region, the amount of condensation, and the pH of the neutralization agent. To facilitate intermittent neutralization agent injection, a timer may be implemented with the invention to cause the system to inject the neutralization agent into the target regions at predetermined intervals. The length of each injection period, e.g., the duration of each injection in the intermittent injection embodiment, also can vary based on a variety of factors such as the pH of the localized condensate, the pH of the neutralization agent, and the amount of condensate in the target region.

FIG. 1 illustrates an MTO reactor and a condensate removal system according to several embodiments of the present invention. As shown, an oxygenate-containing feedstock 101, which preferably contains methanol, is directed to an MTO reactor 102. The oxygenate in the oxygenate-containing feedstock 101 preferably contacts a molecular sieve catalyst in the MTO reactor 102 under conditions effective to convert at least a portion of the oxygenate to light olefins, e.g., ethylene and propylene, which exit the MTO reactor 102 through product stream 103. After optionally being cooled in one or more heat exchangers, not shown, the product stream 103 preferably is introduced into a quench unit 104.

In the quench unit 104, the product stream 103 contacts a quench medium under conditions effective to condense at least a portion of the readily condensable components contained in the product stream 103. Specifically, the product stream 103 contacts the quench medium, preferably in a countercurrent manner, under conditions effective to form a light product fraction 105 and a heavy product fraction 106. The light product fraction 105 preferably contains a majority of the light olefins, more preferably at least 80 weight percent and most preferably at least 95 weight percent of the light olefins that were present in the product stream 103, based on the total weight of the product stream 103 introduced into quench unit 104. The heavy product fraction 106 preferably contains a majority of the water, more preferably at least 80 weight percent and most preferably at least 95 weight percent of the water that was present in the product stream 103, based on the total weight of the product stream 103 introduced into quench unit 104.

The quench unit 104 preferably includes a pumparound outlet adjacent its bottom, whereby a portion of the readily condensable components are removed from the quench unit 104 to form an initial pumparound stream 107, which may be a bottoms stream, not as shown, or a side draw stream, as shown. Initial pumparound stream 107 is pumped by pump 108 to a heat exchanger 110 via pumparound stream 109. Heat exchanger 110 cools pumparound stream 109 thereby forming cooled pumparound stream 111, which preferably is reintroduced into the quench unit 104 at a pumparound inlet, which is oriented at a point on the quench unit 104 higher than the pumparound outlet. The cooled pumparound stream 111 acts as the quench medium to facilitate quenching of product stream 103. As used herein, the terms "pumparound" and "pumparound stream" include one or more of the initial pumparound stream 107, pump 108, pumparound stream 109, heat exchanger 110 and cooled pumparound stream 111. In an alternative embodiment, not shown, the initial pumparound stream 107 and the heavy product fraction 106 are derived from an initial quench unit bottoms stream. That is, an initial quench unit bottoms stream is divided into two streams—the initial pumparound stream 107 and the heavy product fraction 106.

Ideally, the light product fraction 105, or a portion thereof, is directed to a compression system, which preferably includes a plurality of compression stages. Two compression stages, a first compression stage 151 and a second compression stage 152, are illustrated in FIG. 1. Specifically, light product fraction 105, or a portion thereof, is directed to first compressor 129, which compresses at least a portion of light product fraction 105 forming compressed light product stream 130. Compressed light product stream 130 preferably is cooled in intercooler 131 to form cooled light product stream 132. Cooled light product stream 132 is then directed to a knockout drum 133 for separation of liquid components from gaseous components. In one embodiment, at least a portion of the liquid components in knockout drum 133 are removed therefrom via condensate stream 135. In another embodiment, not shown, all or a portion of the aqueous components in knockout drum 133 are removed therefrom and combined with the pumparound stream. Additionally or alternatively, a portion of the aqueous components in knockout drum 133 are removed therefrom and reintroduced directly into the quench unit 104. In another embodiment, not shown, a portion of the aqueous components in knockout drum 133 are removed therefrom and combined with one or more upstream and/or downstream streams in the compression system. Gaseous components from knockout drum 133 form derivative light product stream 136, which preferably is withdrawn from the knockout drum 133 and directed to second compressor 137 in second compression stage 152.

Non-aqueous components may also condense in knock out drum 133. As a result, knockout drum 133 optionally acts as a three phase separation unit. In this embodiment, conditions are effective in knockout drum 133 to separate the cooled light product stream 132 into derivative light product stream 136, an oil stream, not shown, and aqueous condensate stream 135. In this embodiment, knockout drum 133 includes a vapor stream outlet, an aqueous condensate stream outlet, and an oil phase outlet, which ideally is an opening in a conduit that extends through the heavier aqueous layer and withdraws the oil phase from a point above the oil/aqueous interface.

Second compressor 137 compresses at least a portion of the derivative light product stream 136 and forms compressed light product stream 138. Compressed light product stream 138 preferably is cooled in intercooler 139 to form cooled light product stream 153. Cooled light product stream 153 is then directed to a knockout drum 140 for separation of liquid components from gaseous components. In one embodiment, at least a portion of the liquid components in knockout drum 140 are removed therefrom via condensate stream 141. Optionally, a portion of the liquid components in knockout drum 140 are removed therefrom and combined with the pumparound stream, discussed above. Additionally or alternatively, a portion of the liquid components in knockout drum 140 are removed therefrom and reintroduced directly into the quench unit 104. Additionally or alternatively, a portion of the liquid components in knockout drum 140 are removed therefrom and combined with one or more upstream and/or downstream streams in the compression system. The knockout drum 140 optionally acts as a three phase separation unit, as described above with reference to knockout drum 133. Gaseous components from knockout drum 140 form final light product stream 142, which preferably is withdrawn from the knockout drum 140 and directed to a separation system, not shown in FIG. 1. The separation system preferably includes a plurality of separation units and is adapted to separate one or more components contained in the final light product stream 142. Ultimately, the separation system preferably forms polymerization grade ethylene and propylene.

Although FIG. 1 illustrates two compression stages, the present invention is not so limited, and the compression system may include more than two compression stages. If the compression system includes more than two compression stages, the compression system may form a plurality of derivative light product streams, each derivative light product stream being associated with a respective intermediate compressor.

Heavy product fraction 106 from the quench unit 104 preferably is directed to a three-phase separation unit 112 wherein the heavy product fraction 106 is subjected to conditions effective to separate the heavy product fraction 106 into a vapor stream 113, an oil stream 114 and an aqueous stream 115. Preferably, the vapor in vapor stream 113 is redirected to the quench unit 104 for further processing, and the oil in oil stream 114 preferably is directed to one or more separation units, not shown, for further processing or is burned as fuel. The aqueous stream 115 typically contains water, unreacted oxygenates such as methanol and dimethyl ether, aldehydes, organic and inorganic acids and dissolved hydrocarbons. The aqueous stream 115 preferably is directed to a condensate stripper 116 in order to recover any unreacted oxygenates from water.

The condensate stripper 116 preferably is a distillation column, which is adapted to separate unreacted oxygenates from water. In the condensate stripper 116, at least a portion of the heavy product fraction 106, e.g., the aqueous stream 115, is subjected to conditions effective to form an overhead oxygenate stream 122, which preferably contains a majority of the oxygenates that were present in the at least a portion of the heavy product fraction 106, and a stripped water-containing stream 118, which preferably contains a majority of the water that was present in the at least a portion of the heavy product fraction 106.

The condensate stripper 116 optionally includes an overhead condenser system for forming the overhead oxygenate stream 122. As shown, an initial overhead stream 117 from the condensate stripper 116 is directed to heat exchanger 119 for initial overhead stream cooling thereby forming cooled overhead stream 120. The cooled overhead stream 120 is then directed to a knockout drum 121 wherein components are allowed to condense. The condensed components in the knockout drum 121 preferably are withdrawn therefrom via condensed component stream 123, which is redirected to the condensate stripper 116 for further processing. Uncondensed components form the overhead oxygenate stream 122. In a preferred embodiment, not shown in FIG. 1, at least a portion of the overhead oxygenate stream 122 is directed to and combined with feedstock 101 or sent directly to the MTO reactor 102 for further conversion to light olefins.

The condensate stripper 116 also preferably includes a reboiler system. In this embodiment, an optional pump 125 withdraws a stripped reboiler stream 124, e.g., a reboiler bottoms stream, from the condensate stripper 116 and pumps stream 126 to heat exchanger 127 for stripped reboiler stream heating. Alternatively, a thermosiphon, not shown, rather than a pump 125 may be used to withdraw the stripped reboiler stream 124 from the condensate stripper 116. The heat exchanger 127 heats and preferably vaporizes at least a portion of pumped stream 126, thus forming a heated reboiler stream 128. At least a portion of the heated reboiler stream 128 is then redirected to the condensate stripper 116 for further processing. As shown, two bottoms streams are withdrawn in parallel from the condensate stripper 116, the first stream being a stripped water-containing stream 118 and the second stream being the stripped reboiler stream 124. The stripped water-containing stream 118 preferably is directed to a water treatment facility, not shown, for treatment thereof. Alternatively, a single bottoms stream, not shown, is withdrawn from the condensate stripper 116 and is divided between the stripped water-containing stream 118 and the stripped reboiler stream 124.

As discussed above, the present invention is directed to injecting a neutralization agent into one or more regions of the MTO effluent processing system. In one embodiment, the neutralization agent is injected into one or more regions of the pumparound stream, such as the initial pumparound stream 107, the pump 108, pumparound stream 109, heat exchanger 110, and/or cooled pumparound stream 111. FIG. 1 illustrates neutralization agent stream 145 delivering neutralization agent into pumparound stream 109. In another embodiment, not shown, the neutralization agent is injected directly into the quench unit 104 without mixing the neutralization agent with the quench medium prior to the introduction of the neutralization agent into the quench unit 104.

In another embodiment of the present invention, the neutralization agent is injected into one or more regions within the condenser system of the condensate stripper 116. Specifically, the neutralization agent optionally is injected into one or more of the initial overhead stream 117, heat exchanger 119, cooled initial overhead stream 120, knockout drum 121, and/or condensed component stream 123. The neutralization agent also may be injected into overhead oxygenate stream 122. As shown in FIG. 1, neutralization agent is injected into initial overhead stream 117 through neutralization agent stream 148.

In one embodiment, the neutralization agent is injected into one or more regions of the condensate stripper 116. In this embodiment, the neutralization agent preferably is injected into the condensate stripper 116 in a region below the introduction point of the aqueous stream 115 or of heavy product fraction 106. However, it is contemplated that the neutralization agent may be injected into the condensate stripper 116 at a point above this introduction point. The neutralization agent optionally is injected directly into the region of the condensate stripper 116 that contains the packing material, above the packing material or below the packing material. As shown in FIG. 1, neutralization agent is injected into the condensate stripper 116 through neutralization agent stream 149, which is oriented below the packing material. In one embodiment, not shown, the neutralization agent is injected into aqueous stream 115, into three-phase separation unit 112, and/or into heavy product fraction 106 prior to its introduction into the condensate stripper 116.

In another embodiment of the present invention, the neutralization agent is injected into one or more regions within the reboiler system of the condensate stripper 116. Specifically, the neutralization agent optionally is injected into one or more of stripped reboiler stream 124, pump 125 or a thermosiphon (not shown), pumped stream 126, heat exchanger 127, and/or heated reboiler stream 128. As shown in FIG. 1, neutralization agent is injected into stripped reboiler stream 124 through neutralization agent stream 150.

In another embodiment of the present invention, the neutralization agent is injected into one or more regions of the compression system. Specifically, the neutralization agent optionally is injected into one or more of: light product fraction 105, first compressor 129, compressed light product stream 130, intercooler 131, cooled light product stream 132, knockout drum 133, condensate stream 135, derivative light product stream 136, second compressor 137, compressed light product stream 138, intercooler 139, cooled light product stream 153, knockout drum 140, condensate stream 141, and/or final light product stream 142. If the compression system includes more than two compression stages, then the neutralization agent may be injected into one or more corresponding regions of those additional compression stages. As shown in FIG. 1, neutralization agent is injected into compressed light product streams 130 and 138 through neutralization agent stream 146 and neutralization agent stream 147, respectively. Neutralization agent is also shown being injected into light product fraction 105 via neutralization agent stream 144.

Methanol-to-Olefin Reaction Systems

The present invention provides for reducing corrosion in an effluent processing system of an MTO reaction system, which is discussed in more detail hereinafter.

The present invention is useful in a variety of processes including: cracking, of for example a naphtha feed to light olefin(s) (U.S. Pat. No. 6,300,537) or higher molecular weight (MW) hydrocarbons to lower MW hydrocarbons; hydrocracking, of for example heavy petroleum and/or cyclic feedstock; isomerization, of for example aromatics such as xylene; polymerization, of for example one or more olefin(s) to produce a polymer product; reforming; hydrogenation; dehydrogenation; dewaxing, of for example hydrocarbons to remove straight chain paraffins; absorption, of for example alkyl aromatic compounds for separating out isomers thereof; alkylation, of for example aromatic hydrocarbons such as benzene and alkyl benzene, optionally with propylene to produce cumeme or with long chain olefins; transalkylation, of for example a combination of aromatic and polyalkylaromatic hydrocarbons; dealkylation; hydrodecylization; disproportionation, of for example toluene to make benzene and paraxylene; oligomerization, of for example straight and branched chain olefin(s); and dehydrocyclization.

Preferred processes are conversion processes including: naphtha to highly aromatic mixtures; light olefin(s) to gasoline, distillates and lubricants; oxygenates to olefin(s); light paraffins to olefins and/or aromatics; and unsaturated hydrocarbons (ethylene and/or acetylene) to aldehydes for conversion into alcohols, acids and esters. The most preferred process of the invention is a process directed to the conversion of a feedstock comprising one or more oxygenates to one or more olefin(s) in the presence of a molecular sieve catalyst.

Molecular sieves have various chemical and physical, framework, characteristics. Molecular sieves have been well classified by the Structure Commission of the International Zeolite Association according to the rules of the IUPAC Commission on Zeolite Nomenclature. A framework-type describes the connectivity, topology, of the tetrahedrally coordinated atoms constituting the framework, and making an abstraction of the specific properties for those materials. Framework-type zeolite and zeolite-type molecular sieves for which a structure has been established, are assigned a three letter code and are described in the Atlas of Zeolite Framework Types, 5th edition, Elsevier, London, England (2001), which is herein fully incorporated by reference.

Non-limiting examples of these molecular sieves are the small pore molecular sieves, AEI, AFT, APC, ATN, ATT, ATV, AWW, BIK, CAS, CHA, CHI, DAC, DDR, EDI, ER1, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of the preferred molecular sieves, particularly for converting an oxygenate containing feedstock into olefin(s), include AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI framework-type or a CHA framework-type, or a combination thereof, most preferably a CHA framework-type.

Molecular sieve materials all have 3-dimensional framework structure of corner-sharing TO4 tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., Introduction to Zeolite Science and Practice, Second Completely Revised and Expanded Edition, Volume 137, pages 1-67, Elsevier Science, B.V., Amsterdam, Netherlands (2001).

The small, medium and large pore molecular sieves have from a 4-ring to a 12-ring or greater framework-type. In a preferred embodiment, the zeolitic molecular sieves have 8-, 10- or 12-ring structures or larger and an average pore size in the range of from about 3 Å to 15 Å. In the most preferred embodiment, the molecular sieves of the invention, preferably silicoaluminophosphate molecular sieves have 8-rings and an average pore size less than about 5 Å, preferably in the range of from 3 Å to about 5 Å, more preferably from 3 Å to about 4.5 Å, and most preferably from 3.5 Å to about 4.2 Å.

Molecular sieves, particularly zeolitic and zeolitic-type molecular sieves, preferably have a molecular framework of one, preferably two or more corner-sharing [TO4] tetrahedral units, more preferably, two or more [SiO4], [AlO4] and/or [PO4] tetrahedral units, and most preferably [SiO4], [AlO4] and [PO4] tetrahedral units. These silicon, aluminum, and phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 (AlPO4), EP-A-0 158 350 (SENAPSO), U.S. Pat. No. 4,973,460 (Li-APSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit [QO2]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference. Other molecular sieves are described in R. Szostak, Handbook of Molecular Sieves, Van Nostrand Reinhold, New York, N.Y. (1992), which is herein fully incorporated by reference.

The more preferred silicon, aluminum and/or phosphorous containing molecular sieves, and aluminum, phosphorous, and optionally silicon, containing molecular sieves include aluminophosphate (ALPO) molecular sieves and silicoaluminophosphate (SAPO) molecular sieves and substituted, preferably metal substituted, ALPO and SAPO molecular sieves. The most preferred molecular sieves are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthamides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as [MeO2], and carry a net charge depending on the valence state of the metal substitutent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. Patents mentioned above, is represented by the empirical formula, on an anhydrous basis:

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of M, Al and P as tetrahedral oxides, where M is a metal selected from one of Group IA, IIA, IB, IIIB, IVB, VB, VIIB, VIIB, VIIIB and Lanthaide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01. In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and ALPO molecular sieves of the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred zeolite-type molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof.

In an embodiment, the molecular sieve is an intergrowth material having two or more distinct phases of crystalline structures within one molecular sieve composition. In particular, intergrowth molecular sieves are described in the U.S. patent application Ser. No. 09/924,016 filed Aug. 7, 2001 and PCT WO 98/15496 published Apr. 16, 1998, both of which are herein fully incorporated by reference. For example, SAPO-18, ALPO-18 and RUW-18 have an AEI framework-type, and SAPO-34 has a CHA framework-type. In another embodiment, the molecular sieve comprises at least one intergrown phase of AEI and CHA framework-types, preferably the molecular sieve has a greater amount of CHA framework-type to AEI framework-type, and more preferably the ratio of CHA to AEI is greater than 1:1.

The molecular sieve catalyst compositions described above are particularly useful in conversion processes of different feedstock. Typically, the feedstock contains one or more aliphatic-containing compounds that include alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to about 50 carbon atoms, preferably from 1 to 20 carbon atoms, more preferably from 1 to 10 carbon atoms, and most preferably from 1 to 4 carbon atoms.

Non-limiting examples of aliphatic-containing compounds include: alcohols such as methanol and ethanol, alkyl-mercaptans such as methyl mercaptan and ethyl mercaptan, alkyl-sulfides such as methyl sulfide, alkyl-amines such as methyl amine, alkyl-ethers such as dimethyl ether, diethyl ether and methylethyl ether, alkyl-halides such as methyl chloride and ethyl chloride, alkyl ketones such as dimethyl ketone, formaldehydes, and various acids such as acetic acid.

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) or olefin monomer(s) produced from the feedstock typically have from 2 to 30 carbon atoms, preferably 2 to 8 carbon atoms, more preferably 2 to 6 carbon atoms, still more preferably 2 to 4 carbons atoms, and most preferably ethylene an/or propylene. Non-limiting examples of olefin monomer(s) include ethylene, propylene, butene-1, pentene-1,4-methyl-pentene-1, hexene-1, octene-1 and decene-1, preferably ethylene, propylene, butene-1, pentene-1,4-methyl-pentene-1, hexene-1, octene-1 and isomers thereof. Other olefin monomer(s) include unsaturated monomers, diolefins having 4 to 18 carbon atoms, conjugated or nonconjugated dienes, polyenes, vinyl monomers and cyclic olefins.

In the most preferred embodiment, the feedstock, preferably of one or more oxygenates, is converted in the presence of a molecular sieve catalyst composition of the invention into olefin(s) having 2 to 6 carbons atoms, preferably 2 to 4 carbon atoms. Most preferably, the olefin(s), alone or combination, are converted from a feedstock containing an oxygenate, preferably an alcohol, most preferably methanol, to the preferred olefin(s) ethylene and/or propylene.

There are many processes used to convert feedstock into olefin(s) including various cracking processes such as steam cracking, thermal regenerative cracking, fluidized bed cracking, fluid catalytic cracking, deep catalytic cracking, and visbreaking. The most preferred process is generally referred to as gas-to-olefins (GTO) or alternatively, methanol-to-olefins (MTO). In a GTO process, typically natural gas is converted into a synthesis gas that is converted into an oxygenated feedstock, preferably containing methanol, where the oxygenated feedstock is converted in the presence of a molecular sieve catalyst composition into one or more olefin(s), preferably ethylene and/or propylene. In a MTO process, typically an oxygenated feedstock, most preferably a methanol containing feedstock, is converted in the presence of a molecular sieve catalyst composition thereof into one or more olefin(s), preferably and predominantly, ethylene and/or propylene, often referred to as light olefin(s).

In one embodiment of the process for conversion of a feedstock, preferably a feedstock containing one or more oxygenates, the amount of olefin(s) produced based on the total weight of hydrocarbon produced is greater than 50 weight percent, preferably greater than 60 weight percent, more preferably greater than 70 weight percent, and most preferably greater than 75 weight percent. In another embodiment of the process for conversion of one or more oxygenates to one or more olefin(s), the amount of ethylene and/or propylene produced based on the total weight of hydrocarbon product produced is greater than 65 weight percent, preferably greater than 70 weight percent, more preferably greater than 75 weight percent, and most preferably greater than 78 weight percent.

In another embodiment of the process for conversion of one or more oxygenates to one or more olefin(s), the amount ethylene produced in weight percent based on the total weight of hydrocarbon product produced, is greater than 30 weight percent, more preferably greater than 35 weight percent, and most preferably greater than 40 weight percent. In yet another embodiment of the process for conversion of one or more oxygenates to one or more olefin(s), the amount of propylene produced in weight percent based on the total weight of hydrocarbon product produced is greater than 20 weight percent, preferably greater than 25 weight percent, more preferably greater than 30 weight percent, and most preferably greater than 35 weight percent.

The feedstock, in one embodiment, contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, water, is used either in a liquid or a vapor form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, and most preferably from about 5 to about 25.

In one embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process (includes a turbulent bed process), preferably a continuous fluidized bed process, and most preferably a continuous high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference. The preferred reactor type are riser reactors generally described in *Riser Reactor, Fluidization and Fluid-Particle Systems*, pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In the preferred embodiment, a fluidized bed process or high velocity fluidized bed process includes a reactor system, a regeneration system and a recovery system.

The reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a molecular sieve catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol, and the gas is an inert gas such as nitrogen.

In an embodiment, the amount of liquid feedstock fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably of similar or the same composition, or contain varying proportions of the same or different feedstock with the same or different diluent.

The feedstock entering the reactor system is preferably converted, partially or fully, in the first reactor zone into a gaseous effluent that enters the disengaging vessel along with a coked molecular sieve catalyst composition. In the preferred embodiment, cyclone(s) within the disengaging vessel are designed to separate the molecular sieve catalyst composition, preferably a coked molecular sieve catalyst composition, from the gaseous effluent containing one or more olefin(s) within the disengaging zone. Cyclones are preferred, however, gravity effects within the disengaging vessel will also separate the catalyst compositions from the gaseous effluent. Other methods for separating the catalyst compositions from the gaseous effluent include the use of plates, caps, elbows, and the like.

In one embodiment of the disengaging system, the disengaging system includes a disengaging vessel, typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel and the gas is passed at a gas hourly superficial velocity (GHSV) of from 1 $hr^{-1}$ to about 20,000 $hr^{-1}$ based on the volume of gas to volume of coked molecular sieve catalyst composition, preferably at an elevated temperature from 250° C. to about 750° C., preferably from about 350° C. to 650° C., over the coked molecular sieve catalyst composition.

The conversion temperature employed in the conversion process, specifically within the reactor system, is in the range of from about 200° C. to about 1000° C., preferably from about 250° C. to about 800° C., more preferably from about 250° C. to about 750° C., yet more preferably from about 300° C. to about 650° C., yet even more preferably from about 350° C. to about 600° C. most preferably from about 350° C. to about 550° C.

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock containing methanol and dimethyl ether is in the range of from about 20 $hr^{-1}$ to about 300 $hr^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

In one preferred embodiment of the process for converting an oxygenate to olefin(s) using a silicoaluminophosphate molecular sieve catalyst composition, the process is operated at a WHSV of at least 20 $hr^{-1}$ and a Temperature Corrected Normalized Methane Selectivity (TCNMS) of less than 0.016, preferably less than or equal to 0.01. See for example U.S. Pat. No. 5,952,538, which is herein fully incorporated by reference. In another embodiment of the processes for converting an oxygenate such as methanol to one or more olefin(s) using a molecular sieve catalyst composition, the WHSV is from 0.01 $hr^{-1}$ to about 100 $hr^{-1}$, at a temperature of from about 350° C. to 550° C., and silica to $Me_2O_3$ (Me is a Group IIIA or VIII element from the Periodic Table of Elements) molar ratio of from 300 to 2500. See for example EP-0 642 485 B1, which is herein fully incorporated by reference. Other processes for converting an oxygenate such as methanol to one or more olefin(s) using a molecular sieve catalyst composition are described in PCT WO 01/23500 published Apr. 5, 2001 (propane reduction at an average catalyst feedstock exposure of at least 1.0), which is herein incorporated by reference.

The coked molecular sieve catalyst composition is withdrawn from the disengaging vessel, preferably by one or more cyclones(s), and introduced to the regeneration system. The regeneration system comprises a regenerator where the coked catalyst composition is contacted with a regeneration medium, preferably a gas containing oxygen, under general regeneration conditions of temperature, pressure and residence time. Non-limiting examples of the regeneration medium include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. The regeneration conditions are those capable of burning coke from the coked catalyst composition, preferably to a level less than 0.5 weight percent based on the total weight of the coked molecular sieve catalyst composition entering the regeneration system. The coked molecular sieve catalyst composition withdrawn from the regenerator forms a regenerated molecular sieve catalyst composition.

The regeneration temperature is in the range of from about 200° C. to about 1500° C., preferably from about 300° C. to about 1000° C., more preferably from about 450° C. to about 750° C., and most preferably from about 550° C. to 700° C. The regeneration pressure is in the range of from about 15 psia (103 kPaa) to about 500 psia (3448 kPaa), preferably from about 20 psia (138 kPaa) to about 250 psia (1724 kPaa), more preferably from about 25 psia (172 kPaa) to about 150 psia (1034 kPaa), and most preferably from about 30 psia (207 kPaa) to about 60 psia (414 kPaa). The preferred residence time of the molecular sieve catalyst composition in the regenerator is in the range of from about one minute to several hours, most preferably about one minute to 100 minutes, and the preferred volume of oxygen in the gas is in the range of from about 0.01 mole percent to about 5 mole percent based on the total volume of the gas.

In one embodiment, regeneration promoters, typically metal containing compounds such as platinum, palladium and the like, are added to the regenerator directly, or indirectly, for example with the coked catalyst composition. Also, in another embodiment, a fresh molecular sieve catalyst composition is added to the regenerator containing a regeneration medium of oxygen and water as described in U.S. Pat. No. 6,245,703, which is herein fully incorporated by reference. In yet another embodiment, a portion of the coked molecular sieve catalyst composition from the regenerator is returned directly to the one or more riser reactor(s), or indirectly, by pre-contacting with the feedstock, or contacting with fresh molecular sieve catalyst composition, or contacting with a regenerated molecular sieve catalyst composition or a cooled regenerated molecular sieve catalyst composition described below.

The burning of coke is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated molecular sieve catalyst composition from the regeneration system and passing the regenerated molecular sieve catalyst composition through a catalyst cooler that forms a cooled regenerated molecular sieve catalyst composition. The catalyst cooler, in an embodiment, is a heat exchanger that is located either internal or external to the regeneration system. In one embodiment, the cooler regenerated molecular sieve catalyst composition is returned to the regenerator in a continuous cycle, alternatively, (see U.S. patent application Ser. No. 09/587,766 filed Jun. 6, 2000) a portion of the cooled regenerated molecular sieve catalyst composition is returned to the regenerator vessel in a continuous cycle, and another portion of the cooled molecular sieve regenerated molecular sieve catalyst composition is returned to the riser reactor(s), directly or indirectly, or a portion of the regenerated molecular sieve catalyst composition or cooled regenerated molecular sieve catalyst composition is contacted with by-products within the gaseous effluent (PCT WO 00/49106 published Aug. 24, 2000), which are all herein fully incorporated by reference. In another embodiment, a regenerated molecular sieve catalyst composition contacted with an alcohol, preferably ethanol, 1-propnaol, 1-butanol or mixture thereof, is introduced to the reactor system, as described in U.S. patent application Ser. No. 09/785,122 filed Feb. 16, 2001, which is herein fully incorporated by reference. Other methods for operating a regeneration system are in disclosed U.S. Pat. No. 6,290,916 (controlling moisture), which is herein fully incorporated by reference.

The regenerated molecular sieve catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the riser reactor(s). In another embodiment, the regenerated molecular sieve catalyst composition withdrawn from the regeneration system is returned to the riser reactor(s) directly, optionally after passing through a catalyst cooler. In one embodiment, a carrier, such as an inert gas, feedstock vapor, steam or the like, semi-continuously or continuously, facilitates the introduction of the regenerated molecular sieve catalyst composition to the reactor system, preferably to the one or more riser reactor(s).

In one embodiment, the optimum level of coke on the molecular sieve catalyst composition in the reaction zone is maintained by controlling the flow of the regenerated molecular sieve catalyst composition or cooled regenerated molecular sieve catalyst composition from the regeneration system to the reactor system, a complete regeneration. There are many techniques for controlling the flow of a molecular sieve catalyst composition described in Michael Louge, *Experimental Techniques, Circulating Fluidized Beds*, Grace, Avidan and Knowlton, eds., Blackie, 1997 (336-337), which is herein incorporated by reference. In another embodiment, the optimum level of coke on the molecular sieve catalyst composition in the reaction zone is maintained by controlling the flow rate of oxygen containing gas flowing to the regenerator, a partial regeneration. Coke levels on the molecular sieve catalyst composition is measured by withdrawing from the conversion process the molecular sieve catalyst composition at a point in the process and determining its carbon content. Typical levels of coke on the molecular sieve catalyst composition, after regeneration is in the range of from 0.01 weight percent to about 15 weight percent, preferably from about 0.1 weight percent to about 10 weight percent, more preferably from about 0.2 weight percent to about 5 weight percent, and most preferably from about 0.3 weight percent to about 2 weight percent based on the total weight of the molecular sieve and not the total weight of the molecular sieve catalyst composition.

In one preferred embodiment, the mixture of fresh molecular sieve catalyst composition and/or regenerated molecular sieve catalyst composition and/or cooled regenerated molecular sieve catalyst composition in the reaction zone contains in the range of from about 1 to 50 weight percent, preferably from about 2 to 30 weight percent, more preferably from about 2 to about 20 weight percent, and most preferably from about 2 to about 10 coke or carbonaceous deposit based on the total weight of the mixture of molecular sieve catalyst compositions. See for example U.S. Pat. No. 6,023,005, which is herein fully incorporated by reference. It is recognized that the molecular sieve catalyst composition in the reaction zone is made up of a mixture of regenerated and fresh molecular sieve catalyst composition that have varying levels of carbon and carbon-like deposits, coke. The measured level of these deposits, specifically coke, represents an average of the levels on individual molecular sieve catalyst composition particles.

The gaseous effluent is withdrawn from the disengaging system and is passed through a recovery system. There are many well known recovery systems, techniques and sequences that are useful in separating olefin(s) and purifying olefin(s) from the gaseous effluent. Recovery systems generally comprise one or more or a combination of separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment for example various condensers, heat exchangers, refrigeration systems or chill trains, compressors, knockout drums or pots, pumps, and the like. Non-limiting examples of these towers, columns, splitters or trains used alone or in combination include one or more of a demethanizer, preferably a high temperature demethanizer, a deethanizer, a depropanizer, preferably a wet depropanizer, a wash tower often referred to as a caustic wash tower and/or quench tower, absorbers, adsorbers, membranes, ethylene (C2) splitter, propylene (C3) splitter, butene (C4) splitter, and the like.

Various recovery systems useful for recovering predominately olefin(s), preferably prime or light olefin(s) such as ethylene, propylene and/or butene are described in U.S. Pat. No. 5,960,643 (secondary rich ethylene stream), U.S. Pat. Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No. 6,121, 504 (direct product quench), U.S. Pat. No. 6,121,503 (high purity olefins without superfractionation), and U.S. Pat. No. 6,293,998 (pressure swing adsorption), which are all herein fully incorporated by reference.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants. Non-limiting examples of contaminants and by-products include generally polar compounds such as water, alcohols, carboxylic acids, ethers, carbon oxides, sulfur compounds such as hydrogen sulfide, carbonyl sulfides and mercaptans, ammonia and other nitrogen compounds, arsine, phosphine and chlorides. Other contaminants or by-products include hydrogen and hydrocarbons such as acetylene, methyl acetylene, propadiene, butadiene and butyne.

Other recovery systems that include purification systems, for example for the purification of olefin(s), are described in Kirk-*Othmer Encyclopedia of Chemical Technology, 4th Edition*, Volume 9, John Wiley & Sons, 1996, pages 249-271 and 894-899, which is herein incorporated by reference. Purification systems are also described in for example, U.S. Pat. No. 6,271,428 (purification of a diolefin hydrocarbon stream), U.S. Pat. No. 6,293,999 (separating propylene from propane), and U.S. patent application Ser. No. 09/689,363 filed Oct. 20, 2000 (purge stream using hydrating catalyst), which is herein incorporated by reference.

Typically, in converting one or more oxygenates to olefin(s) having 2 or 3 carbon atoms, an amount of hydrocarbons, particularly olefin(s), especially olefin(s) having 4 or more carbon atoms, and other by-products are formed or produced. Included in the recovery systems of the invention are reaction systems for converting the products contained within the effluent gas withdrawn from the reactor or converting those products produced as a result of the recovery system utilized.

In one embodiment, the effluent gas withdrawn from the reactor is passed through a recovery system producing one or more hydrocarbon containing stream(s), in particular, a three or more carbon atom (C3+) hydrocarbon containing stream. In this embodiment, the C3+ hydrocarbon containing stream is passed through a first fractionation zone producing a crude C3 hydrocarbon and a C4+ hydrocarbon containing stream, the C4+ hydrocarbon containing stream is passed through a second fractionation zone producing a crude C4 hydrocarbon and a C5+ hydrocarbon containing stream. The four or more carbon hydrocarbons include butenes such as butene-1 and butene-2, butadienes, saturated butanes, and isobutanes.

The effluent gas removed from a conversion process, particularly a MTO process, typically has a minor amount of hydrocarbons having 4 or more carbon atoms. The amount of hydrocarbons having 4 or more carbon atoms is typically in an amount less than 20 weight percent, preferably less than 10 weight percent, more preferably less than 5 weight percent, and most preferably less than 2 weight percent, based on the total weight of the effluent gas withdrawn from a MTO process, excluding water. In particular with a conversion process of oxygenates into olefin(s) utilizing a molecular sieve catalyst composition the resulting effluent gas typically comprises a majority of ethylene and/or propylene and a minor amount of four carbon and higher carbon number products and other by-products, excluding water.

Suitable well known reaction systems as part of the recovery system primarily take lower value products and convert them to higher value products. For example, the C4 hydrocarbons, butene-1 and butene-2 are used to make alcohols having 8 to 13 carbon atoms, and other specialty chemicals, isobutylene is used to make a gasoline additive, methyl-t-butylether, butadiene in a selective hydrogenation unit is converted into butene-1 and butene-2, and butane is useful as a fuel. Non-limiting examples of reaction systems include U.S. Pat. No. 5,955,640 (converting a four carbon product into butene-1), U.S. Pat. No. 4,774,375 (isobutane and butene-2 oligomerized to an alkylate gasoline), U.S. Pat. No. 6,049,017 (dimerization of n-butylene), U.S. Pat. Nos. 4,287,369 and 5,763,678 (carbonylation or hydroformulation of higher olefins with carbon dioxide and hydrogen making carbonyl compounds), U.S. Pat. No. 4,542,252 (multistage adiabatic process), U.S. Pat. No. 5,634,354 (olefin-hydrogen recovery), and Cosyns, J. et al., Process for Upgrading C3, C4 and C5 Olefinic Streams, Pet. & Coal, Vol. 37, No. 4 (1995) (dimerizing or oligomerizing propylene, butylene and pentylene), which are all herein fully incorporated by reference.

The preferred light olefin(s) produced by any one of the processes described above, preferably conversion processes, are high purity prime olefin(s) products that contains a single carbon number olefin in an amount greater than 80 percent, preferably greater than 90 weight percent, more preferably greater than 95 weight percent, and most preferably no less than about 99 weight percent, based on the total weight of the olefin. In one embodiment, high purity prime olefin(s) are produced in the process of the invention at rate of greater than 5 kg per day, preferably greater than 10 kg per day, more preferably greater than 20 kg per day, and most preferably greater than 50 kg per day. In another embodiment, high purity ethylene and/or high purity propylene is produced by the process of the invention at a rate greater than 4,500 kg per day, preferably greater than 100,000 kg per day, more preferably greater than 500,000 kg per day, even more preferably greater than 1,000,000 kg per day, yet even more preferably greater than 1,500,000 kg per day, still even more preferably greater than 2,000,000 kg per day, and most preferably greater than 2,500,000 kg per day.

Other conversion processes, in particular, a conversion process of an oxygenate to one or more olefin(s) in the presence of a molecular sieve catalyst composition, especially where the molecular sieve is synthesized from a silicon-,phosphorous-, and alumina-source, include those described in for example: U.S. Pat. No. 6,121,503 (making plastic with an olefin product having a paraffin to olefin weight ratio less than or equal to 0.05), U.S. Pat. No. 6,187,983 (electromagnetic energy to reaction system), PCT WO 99/18055 publishes Apr. 15, 1999 (heavy hydrocarbon in effluent gas fed to another reactor) PCT WO 01/60770 published Aug. 23, 2001 and U.S. patent application Ser. No. 09/627,634 filed July 28, 2000 (high pressure), U.S. patent application Ser. No. 09/507,838 filed Feb. 22, 2000 (staged feedstock injection), and U.S. patent application Ser. No. 09/785,409 filed Feb. 16, 2001 (acetone co-fed), which are all herein fully incorporated by reference.

One embodiment of the MTO system provides an integrated process of producing light olefin(s) from a hydrocarbon feedstock, preferably a hydrocarbon gas feedstock, more preferably methane and/or ethane. The first step in the process is passing the gaseous feedstock, preferably in combination with a water stream, to a syngas production zone to produce a synthesis gas (syngas) stream. Syngas production is well known, and typical syngas temperatures are in the range of from about 700° C. to about 1200° C. and syngas pressures are in the range of from about 2 MPa to about 100 MPa. Synthesis gas streams are produced from natural gas, petroleum liquids, and carbonaceous materials such as coal, recycled plastic, municipal waste or any other organic material, preferably synthesis gas stream is produced via steam reforming of natural gas. Generally, a heterogeneous catalyst, typically a copper based catalyst, is contacted with a synthesis gas stream, typically carbon dioxide and carbon monoxide and hydrogen to produce an alcohol, preferably methanol, often in combination with water. In one embodiment, the synthesis gas stream at a synthesis temperature in the range of from about 150° C. to about 450° C. and at a synthesis pressure in the range of from about 5 MPa to about 10 MPa is passed through a carbon oxide conversion zone to produce an oxygenate containing stream.

This oxygenate containing stream, or crude methanol, typically contains the alcohol product and various other components such as ethers, particularly dimethyl ether, ketones, aldehydes, dissolved gases such as hydrogen methane, carbon oxide and nitrogen, and fusel oil. The oxygenate containing stream, crude methanol, in the preferred embodiment is passed through well known purification processes, distillation, separation and fractionation, resulting in a purified oxygenate containing stream, for example, commercial Grade A and AA methanol. The oxygenate containing stream or purified oxygenate containing stream, optionally with one or more diluents, is contacted with one or more molecular sieve catalyst composition described above in any one of the processes described above to produce a variety of prime products, particularly light olefin(s), ethylene and/or propylene. Non-limiting examples of this integrated process is described in EP-B-0 933 345, which is herein fully incorporated by reference. In another more fully integrated process, optionally with the integrated processes described above, olefin(s) produced are directed to, in one embodiment, one or more polymerization processes for producing various polyolefins. (See for example U.S. patent application Ser. No. 09/615,376 filed Jul. 13, 2000, which is herein fully incorporated by reference.)

Polymerization processes include solution, gas phase, slurry phase and a high pressure processes, or a combination thereof. Particularly preferred is a gas phase or a slurry phase polymerization of one or more olefin(s) at least one of which is ethylene or propylene. These polymerization processes utilize a polymerization catalyst that can include any one or a combination of the molecular sieve catalysts discussed above, however, the preferred polymerization catalysts are those Ziegler-Natta, Phillips-type, metallocene, metallocene-type and advanced polymerization catalysts, and mixtures thereof. The polymers produced by the polymerization processes described above include linear low density polyethylene, elastomers, plastomers, high density polyethylene, low density polyethylene, polypropylene and polypropylene copolymers. The propylene based polymers produced by the polymerization processes include atacetic polypropylene, isotacetic polypropylene, syndiotacetic polypropylene, and propylene random, block or impact copolymers.

In preferred embodiment, the integrated process comprises a polymerizing process of one or more olefin(s) in the presence of a polymerization catalyst system in a polymerization reactor to produce one or more polymer products, wherein the one or more olefin(s) having been made by converting an alcohol, particularly methanol, using a molecular sieve catalyst composition. The preferred polymerization process is a gas phase polymerization process and at least one of the olefins(s) is either ethylene or propylene, and preferably the polymerization catalyst system is a supported metallocene catalyst system. In this embodiment, the supported metallocene catalyst system comprises a support, a metallocene or metallocene-type compound and an activator, preferably the activator is a non-coordinating anion or alumoxane, or combination thereof, and most preferably the activator is alumoxane.

In addition to polyolefins, numerous other olefin derived products are formed from the olefin(s) recovered any one of the processes described above, particularly the conversion processes, more particularly the GTO process or MTO process. These include, but are not limited to, aldehydes, alcohols, acetic acid, linear alpha olefins, vinyl acetate, ethylene dicholoride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes.

Figure 2:
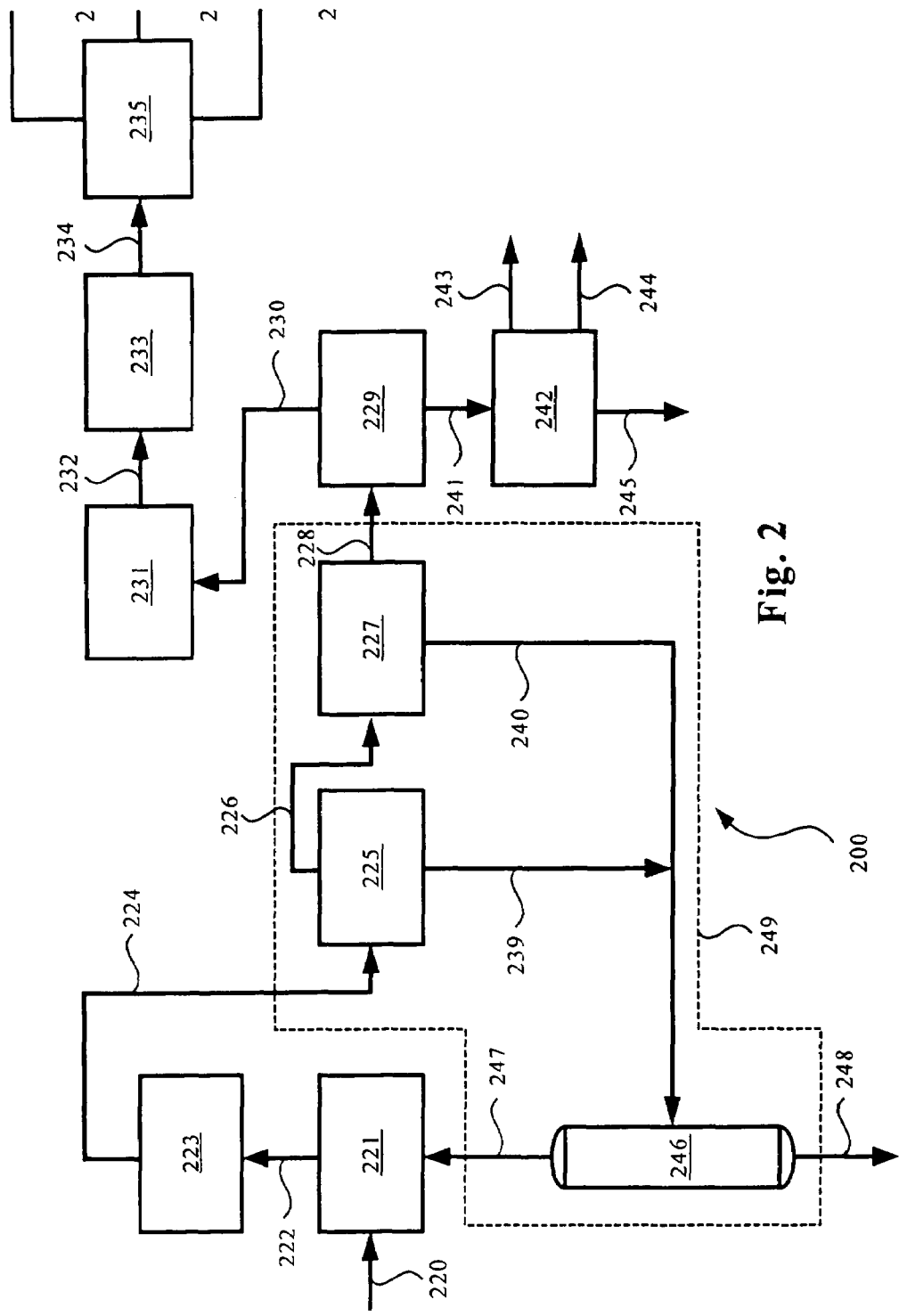
FIG. 2 illustrates a flow diagram of a methanol-to-olefin reaction system including a condensate removal system.

FIG. 2 is a flow diagram illustrating an MTO reaction system, generally designated 200, and will now be described in greater detail. A methanol-containing feedstock or feed stream 220 is fed to a feed vaporization and introduction (FVI) system 221, which subjects the methanol in the methanol-containing feed stream 220 to conditions, e.g., temperature and pressure, sufficient to at least partially vaporize the methanol. For example, the FVI system preferably includes a vapor-liquid disengaging drum, in which conditions are sufficient to provide a vaporized methanol-containing stream 222 and a liquid stream, not shown, which may include non-volatiles. The vaporized methanol-containing stream 222 is directed to MTO reactor unit 223, in which the methanol in vaporized methanol-containing stream 222 contacts an MTO catalyst under conditions effective to convert at least a portion of the methanol to light olefins in product stream 224. Light olefins product stream 224 includes methane, ethylene, ethane, propylene, propane, DME, C4 olefins, C5+ hydrocarbons, water and other hydrocarbon components.

The light olefins product stream 224 preferably is then directed to a quench unit 225, e.g., a quench tower, wherein the light olefins product stream 224 is cooled and water and other readily condensable components are condensed. The condensed components, which comprise a substantial amount of water, are withdrawn from the quench unit 225 through a heavy product fraction 239. A portion of the condensed components are circulated through a pumparound stream, not shown, back to the top of the quench unit 225. The pumparound stream may contain a cooling unit, e.g., a heat exchanger, not shown, to further cool the condensed components so as to provide a cooling medium to further cool the components in quench unit 225.

Olefin vapor leaves through the overhead portion of quench unit 225 through light product fraction 226. The olefin vapor in light product fraction 226 is compressed in one or more stages and one or more compressors in compression zone 227 to form a compressed product stream 228, e.g., final light product stream 142 of FIG. 1. After each of one or more stages, the compressed streams pass through heat exchangers and are cooled in order to condense out heavier components such as residual water. The condensed component(s) are collected in one or more knockout drums between compression stages and exit the compression zone 227 via compression condensate stream(s) 240. Compressed product stream 228 optionally passes through a water absorption unit, not shown, where methanol is preferably used as a water absorbent. In the water absorption unit, the water absorbent contacts the compressed product stream 228, preferably in a countercurrent manner, under conditions effective to separate water from the other components in the compressed product stream 228. The light olefins are recovered from the water absorption unit in an overhead stream, not shown. As shown, the compressed product stream 228, or a portion thereof, is directed to a separation system for separating the various components contained therein.

A variety of separation systems may be implemented in accordance with the present invention. U.S. patent application Ser. Nos. 10/125,138, filed Apr. 18, 2002, and Ser. No. 10/124,859, also filed Apr. 18, 2002, the entireties of which are incorporated herein by reference, describe two separation schemes which may be implemented in accordance with the present invention. One non-limiting separation system is illustrated in FIG. 2. As shown, compressed product stream 228 is directed to a C3− separation zone 229. The C3− separation zone 229 separates ethylene and propylene, as well as lighter components, from the DME and heavier components, including C4 olefins, C5+ hydrocarbons, unreacted methanol, and methanol remaining from the optional water absorption unit. The C3− separation zone 229 includes one or more separation units, e.g., distillation columns, which are adapted to separate C3− components from the DME and heavier components. Additional methanol, not shown, optionally is added to the C3− separation zone 229 to reduce hydrate and/or free water formation. A majority of the ethylene and propylene from compressed product stream 228 exits the C3− separation zone 229 via C3− overhead stream 230. A majority of the DME and heavier components, which include C4+ olefins and C5+ hydrocarbons, exits the C3− separation zone 229 through C4+ bottoms stream 241.

The C3− components in C3− overhead stream 230 preferably are directed to a caustic wash unit 231, in which the C3− overhead stream 230 contacts a caustic wash medium under conditions effective to remove carbon dioxide and carbonic acid therefrom and form CO2 depleted stream 232. Preferably, the caustic wash medium is sent through a line, not shown, to the top portion of the caustic wash unit 231 to remove carbon dioxide, which is entrained in the C3− overhead stream 230. Spent caustic leaves the caustic wash unit 231 through a waste caustic line, not shown.

As the present invention is directed to injecting a neutralization agent, e.g., caustic, into one or more target regions of an MTO effluent processing system, the MTO effluent processing system may or may not necessarily include a separate caustic wash unit 231. An additional benefit of the present invention is that the caustic wash unit may be eliminated from an MTO effluent processing system if sufficient neutralization agent was injected to remove carbon dioxide and carbonic acid from the C3− overhead stream 230.

If the separation system includes caustic wash unit 231, then caustic treated ethylene and propylene exits caustic wash unit 231 through CO2 depleted stream 232 and preferably is directed to a water wash column, not shown. Water enters the water wash column and water and absorbed components exit the water wash column through a bottoms line, not shown. Water washed ethylene and propylene exit the water wash column through an overhead line, not shown, and pass through a drying section. As shown, however, CO2 depleted stream 232 from caustic wash unit 231 is directed to drying section 233. Dry product stream 234 exits the drying section 233 and is directed to a C2/C3 separation system 235, which preferably includes one or more cryogenic fractionation columns. The C2/C3 separation system 235 preferably forms a tail gas stream 236, an ethylene product stream 237, and a propylene product stream 238. The tail gas stream 236 preferably includes the majority of the methane and hydrogen that was present in the dry product stream 234; the ethylene product stream 237 preferably includes a majority of the ethylene that was present in the dry product stream 234; and the propylene product stream 238 preferably includes a majority of the propylene that was present in the dry product stream 234. The ethylene and/or propylene in the ethylene product stream 237 and propylene product stream 238, respectively, may be used as monomers or comonomers for the formation of polyethylene and/or polypropylene. The tail gas stream 236 optionally is burned as a fuel in one or more of the steps of the MTO reaction process.

As shown, C4+ bottoms stream 241 from C3− separation zone 229 is directed to a C4/C5+ separation zone 242. The C4/C5+ separation zone 242 includes one or more separation devices, e.g., distillation towers, which separate the C4 olefins from C5+ hydrocarbons in the C4+ bottoms stream 241, thereby forming C4 product stream 243 and C5+ product stream 244. The C4/C5+ separation zone 242 also forms a methanol-containing stream 245, which preferably includes water, unreacted methanol from the vaporized methanol-containing stream 222, methanol from an upstream water absorption unit, if any, DME, and other oxygenate components. Ideally, methanol-containing stream 245 includes a majority of the methanol and water that was present in the C4+ bottoms stream 241.

Heavy product fraction 239, more preferably an aqueous portion thereof, and/or compressor condensate stream(s) 240, alone or in combination, are directed to a condensate separation unit 246, e.g., a condensate stripper. Additionally or alternatively, methanol-containing stream 245 is directed to the condensate separation unit 246. Optionally, heavy product fraction 239 and compressor condensate stream(s) 240 are combined and directed to the condensate separation unit 246 in a single line, as illustrated in FIG. 2. The condensate separation unit 246 preferably includes one or more separation devices, e.g., distillation towers, which subject one or more of the heavy product fraction 239, compressor condensate stream(s) 240 and/or methanol-containing stream 245 to conditions effective to separate the methanol and oxygenated hydrocarbon byproducts from the water contained therein. The condensate separation unit 246 thus forms an overhead oxygenate stream 247, which includes a majority of the methanol that was present in the one or more stream(s) that were directed to the condensate separation unit 246. Preferably, at least a portion of the overhead oxygenate stream 247 is redirected to the FVI system 221 for vaporization, introduction into MTO reactor unit 223, and conversion to light olefins. The condensate separation unit 246 also forms a stripped water-containing stream 248 which includes a majority of the water that was present in the one or more stream(s) that were directed to the condensate separation unit 246.

As disclosed herein, the present invention is directed to reducing corrosion in an MTO effluent processing system. As discussed in detail above with reference to FIG. 1, in a preferred embodiment, the invention is directed to reducing corrosion in the condensate removal system of an MTO effluent processing system. As used herein, the term "condensate removal system" includes the components from the quench unit 225 to the condensate separation unit 246, and including compression zone 227. The condensate removal system in FIG. 2 is outlined by broken line 249.

The present corrosion minimization processes may be implemented in a variety of other process as well. Preferred processes are conversion and/or recovery processes including: converting naphtha to highly aromatic mixtures; converting light olefin(s) to gasoline, distillates and lubricants; converting oxygenates to olefin(s); converting light paraffins to olefins and/or aromatics; converting unsaturated hydrocarbons (ethylene and/or acetylene) to aldehydes for conversion into alcohols, acids and esters; cracking diesel and/or heavy hydrocarbons by cat and/or steam cracking; olefinic recovery trains; and processing streams derived from the pyrolysis of hydrocarbons. The most preferred process of the invention is a process directed to the conversion of a feedstock comprising one or more oxygenates to one or more olefin(s).

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for reducing corrosion in an MTO reactor system, the process comprising the steps of:
   (a) contacting a product stream from an MTO reactor with a quench medium in a quench unit under conditions effective to form a first overhead stream and a first bottoms stream, wherein the first overhead stream comprises light olefins, and wherein the first bottoms stream comprises the quench medium and condensed oxygenates;
   (b) directing at least a portion of the first bottoms stream to a condensate stripper;
   (c) heating the at least a portion of the first bottoms stream in the condensate stripper under conditions effective to form a second overhead stream and a second bottoms stream, wherein the second overhead stream contains recovered oxygenates, and wherein the second bottoms stream contains stripped quench medium;
   (d) partially vaporizing at least a portion of the second bottoms stream to form a vaporized phase and a liquid phase, wherein the liquid phase has a pH;
   (e) adding a neutralization agent to the liquid phase to form a treated stream having a pH greater than the pH of the liquid phase;
   (f) compressing the light olefins in the first overhead stream to form a compressed product fraction:
   (g) directing the compressed product fraction to a $C_{3-}$ separation zone and forming a $C_{3-}$ overhead stream and a $C_{4+}$ bottoms stream; and
   (h) contacting at least a portion of the $C_{3-}$ overhead stream with caustic in a caustic wash unit and forming a caustic unit overhead stream and a caustic unit bottoms stream, wherein the caustic unit overhead stream contains a majority of the light olefins that were present in the light product fraction, and wherein the caustic unit bottoms stream contains at least partially spent caustic.

2. The process of claim 1, wherein the neutralization agent is selected from the group consisting of: caustic, ammonium hydroxide, potassium hydroxide, ammonia and amines.

3. The process of claim 1, wherein the treated stream has a pH of at least 6.0.

4. The process of claim 3, wherein the treated stream has a pH of at least 7.0.

5. The process of claim 1, wherein the process further comprises the step of directing the treated stream and the vaporized stream into the condensate stripper.

6. The process of claim 5, the process further comprising the step of monitoring the pH of the liquid phase.

7. The process of claim 6, wherein the contacting of the neutralization agent is responsive to a determination in that the pH of the liquid phase is approaching acidic conditions.

8. A process for reducing corrosion in an MTO effluent processing system, the process comprising the steps of:
   (a) contacting a product stream from an MTO reactor with a quench medium in a quench unit under conditions effective to form a first overhead stream and a first bottoms stream, wherein the first overhead stream comprises light olefins, and wherein the first bottoms stream comprises the quench medium and condensed oxygenates;
   (b) directing at least a portion of the first bottoms stream to a condensate stripper;
   (c) heating the at least a portion of the first bottoms stream in the condensate stripper under conditions effective to form a second overhead stream and a second bottoms stream, wherein the second overhead stream contains recovered oxygenates, and wherein the second bottoms stream contains stripped quench medium;
   (d) cooling the second overhead stream under conditions effective to partially condense the second overhead stream and form a condensed stream having a pH;
   (e) contacting a neutralization agent with the condensed stream to form a treated stream, wherein the treated stream has a pH greater than the pH of the condensed streams
   (f) compressing the light olefins in the first overhead stream to form a compressed product fraction;
   (g) directing the compressed product fraction to a $C_{3-}$ separation zone and forming a $C_{3-}$ overhead stream and a $C_{4+}$ bottoms stream; and
   (h) contacting at least a portion of the $C_{3-}$ overhead stream with caustic in a caustic wash unit and forming a caustic unit overhead stream and a caustic unit bottoms stream, wherein the caustic unit overhead stream contains a majority of the light olefins that were present in the light product fraction, and wherein the caustic unit bottoms stream contains at least partially spent caustic.

9. The process of claim 8, wherein the neutralization agent is selected from the group consisting of: caustic, ammonium hydroxide, potassium hydroxide, ammonia and amines.

10. The process of claim 8, wherein the treated stream has a pH of at least 6.0.

11. The process of claim 10, wherein the treated stream has a pH of at least 7.0.

12. The process of claim 8, wherein the process further comprises the step of monitoring the pH of the condensed stream.

13. The process of claim 12, wherein the contacting of the neutralization agent is responsive to a determination in that the pH of the condensed stream is approaching acidic conditions.

14. The process of claim 8, wherein the process further comprises the step of monitoring the formation of one or more corrosion sites in a second overhead stream conduit, wherein the second overhead stream conduit contains the condensed stream.

15. The process of claim 14, wherein the contacting of the neutralization agent occurs upstream of the one or more corrosion sites detected in the monitoring of the formation of the one or more corrosion sites.

16. The process of claim 14, wherein the monitoring of the formation of the one or more corrosion sites comprises inserting a corrosion-detection probe into an opening in the second overhead stream conduit, wherein the corrosion-detection probe detects corrosion inside the second overhead stream conduit.

17. The process of claim 16, wherein the corrosion-detection probe is a corrosion coupon.

18. The process of claim 14, wherein the neutralization agent forms a film on an inner surface of the second overhead stream conduit.

* * * * *